US008110599B2

(12) United States Patent
Fan

(10) Patent No.: US 8,110,599 B2
(45) Date of Patent: Feb. 7, 2012

(54) AMPELOPSIN UNSATURATED SODIUM SALT PREPARATION AND APPLICATIONS THEREOF

(76) Inventor: Fulin Fan, Guangzhou (CN)

( * ) Notice: Subject to any disclaimer, the term of this patent is extended or adjusted under 35 U.S.C. 154(b) by 665 days.

(21) Appl. No.: 12/295,479

(22) PCT Filed: Mar. 31, 2006

(86) PCT No.: PCT/CN2006/000581
§ 371 (c)(1),
(2), (4) Date: Sep. 30, 2008

(87) PCT Pub. No.: WO2007/115430
PCT Pub. Date: Oct. 18, 2007

(65) Prior Publication Data
US 2009/0054518 A1 Feb. 26, 2009

(51) Int. Cl.
*A61K 31/352* (2006.01)
*C07D 311/32* (2006.01)
(52) U.S. Cl. ..................... 514/456; 549/400
(58) Field of Classification Search .......... 549/400; 514/456
See application file for complete search history.

(56) References Cited

FOREIGN PATENT DOCUMENTS
CN 1673223 A 9/2005
JP 2003-128664 A 5/2003

OTHER PUBLICATIONS

International Search Report of PCT/CN2006/000581, dated Jan. 18, 2007.
Ruan et al. Improving the solubility of ampelopsin by solid dispersions and inclusion complexes.: Journal of Biomedical Analysis, 38, 2005, pp. 457-564.
Supplementary European Search Report issued by the European Patent Office Sep. 30, 2009 in application No. EP 06 72 2233.
Ruan et al. "Improving the solubility of ampelopsin by solid dispersions and inclusion complexes." Journal of Pharmaceutical and Biomedical Analysis, vol. 38 No. 3, Jul. 1, 2005, pp. 457-464.
Berge et al. "Pharmaceutical Salts." Journal of Pharmaceutical Sciences. vol. 66 No. 1, Jan. 1, 1977, pp. 1-19.

*Primary Examiner* — Bernard Dentz
(74) *Attorney, Agent, or Firm* — Hamre, Schumann, Mueller & Larson, P.C.

(57) ABSTRACT

The present application relates to a novel AMPelopsin unsaturated sodium salt compound (AMP-Na), a method for preparing the same and the applications thereof. The physicochemical properties of AMP-Na according to the present application are significantly altered compared to those of AMPelopsin (AMP). AMP-Na shows significantly reduced toxicity than AMP as evidenced by the in vivo acute toxicity studies. As demonstrated by pharmacological evaluation, AMP-Na exhibits synergistic action when administered in combination with clinically used anti-cancer drugs, therefore reducing their dosages without compromising their therapeutic effects.

10 Claims, 1 Drawing Sheet

US 8,110,599 B2

AMPELOPSIN UNSATURATED SODIUM SALT PREPARATION AND APPLICATIONS THEREOF

TECHNICAL FIELD

The present invention relates to the field of pharmaceutical; particularly, relates to a novel AMPelopsin unsaturated sodium salt compound, its preparation method and applications.

BACKGROUND ART

AMPelopsin (AMP) is a known chemical compound extracted from plant. Its molecular formula is $C_{15}H_{12}O_8 \cdot 2H_2O$ and its structural formula is as follows:

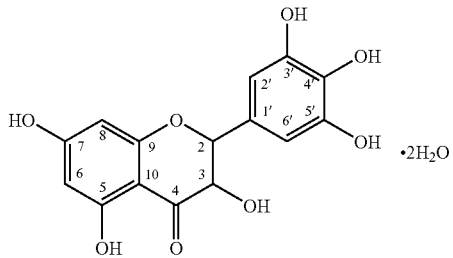

AMP is confirmed to possess anti-cancer properties in pharmacological studies. It can also be used with other anti-cancer drugs to significantly reduce the dosage of other anti-cancer drugs, thus minimizing the side effects of the anti-cancer drugs.

However, there are some major difficulties in the clinical application of AMP, because of its low water solubility. Use of organic reagents, such as isopropanol, DMSO, and DMF, is usually required to enhance its solubility. Due to their high toxicity, these organic reagents are usually unsafe for clinical use. In addition, AMP itself reveals certain toxicity, which limits its safe use in drug development.

Therefore, it is deemed highly necessary for this field to develop a new method to improve the water solubility of AMP and reduce its toxicity.

CONTENTS OF THE INVENTION

The object of the present invention is to provide a novel formula and its preparation method to improve the water solubility of AMP and reduce its toxicity.

In a first aspect, the present invention provides a novel AMPelopsin salt compound and its derivatives, wherein the AMPelopsin salt is obtained by substitution of the hydrogen atoms on AMPelopsin with univalent cations, and the substitution is unsaturated.

In another preferred embodiment, the derivative is a hydrate, or solvate;

In another preferred embodiment, the AMPelopsin salt is represented by formula (I):

$$C_{15}H_6O_8H_\alpha M_\beta \quad (I)$$

wherein,

M is a univalent cation selected from $Li^+$, $K^+$, $Na^+$, $NH_4^+$ or a combination thereof;

$\alpha + \beta = 6$, and $2 \leq \beta \leq 5$.

In another preferred embodiment, M in the formula is Na.

In another preferred embodiment, the AMPelopsin salt is a dihyrate or pentahydrate of the AMPelopsin unsaturated sodium salt.

In another preferred embodiment, the derivative is a pentahydrate of the AMPelopsin unsaturated sodium salt, wherein $\alpha=2$ and $\beta=4$; its molecular formula is: $C_{15}H_8O_8Na_4 \cdot 5H_2O$ and is represented by the following structural formula:

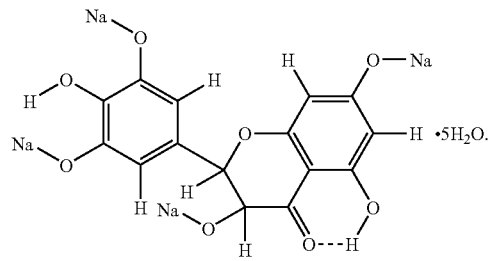

In a second aspect, the present invention provides a method for preparing the AMPelopsin salt and its derivatives, which comprises:

(a) reacting AMPelopsin with the salt-forming agent of formula II to form a AMPelopsin salt of formula I;

$$AMPelopsin + M_m Z \rightarrow C_{15}H_6O_8H_\alpha H_\beta$$

formula II  formula I wherein

M is a univalent cation selected from $Li^+$, $K^+$, $Na^+$, $NH_4^+$ or a combination thereof;

Z is an anion selected from $HCO_3^-$, $CO_3^{2-}$, $PO_4^{3-}$, $HPO_4^{2-}$, $H_2PO_4^-$, $Ac^-$, or a combination thereof;

n=1, 2, or 3;

$\alpha+\beta=6$, and $2 \leq \beta \leq 5$.

the molar ratio of AMPelopsin to M in the salt-forming agent in step (a) is ranged from 1:2 to 1:5; and (b) separating the obtained AMPelopsin salt or its hydrate.

In another preferred embodiment, the salt-forming agent is selected from: sodium bicarbonate, sodium carbonate or a combination thereof.

In another preferred embodiment, the reaction of step (a) is performed in water or aqueous solvents at a temperature of 4~80° C.

In a third aspect, the invention provides a pharmaceutical composition comprising said AMPelopsin salt or its derivatives and pharmaceutically acceptable salt.

In another preferred embodiment, the pharmaceutical composition is selected from injection, solution, tablet, lyophilized powder or capsule.

In another preferred embodiment, the pharmaceutical composition contains 0.2 ug~500 mg/ml of the AMPelopsin salt.

In another preferred embodiment, the pharmaceutical composition comprises additional anti-cancer drugs.

In another preferred embodiment, the additional anti-cancer drugs are selected from carboplatin, 5-FU, doxorubicin, CTX, colchicines, or a combination thereof.

In a fourth aspect of the invention, a method for the treatment of cancers is provided, which comprises the step of administrating an effective and safe amount of the AMPelopsin salt or its derivatives of the present invention to a subject in need of such a treatment.

In another preferred embodiment, the method also further comprises the step of administrating additional anti-cancer drugs before, during, or after the administration of AMPelopsin salt or its derivatives.

In another preferred embodiment, the effective and safe amount of the AMPelopsin salt or its derivatives is 1-5000 mg/person/time.

In a fifth aspect of the present invention, a method for preparing the pharmaceutical composition is presented, which comprises:

(a) mixing AMPelopsin or its derivatives of formula I with pharmaceutically acceptable carriers to form a pharmaceutical composition:

$$C_{15}H_6O_8H_\alpha M_\beta \qquad (I)$$

wherein

M is a univalent cation selected from $Li^+$, $K^+$, $Na^+$, $NH_4^+$ or a combination thereof;

$\alpha+\beta=6$, and $2\leq\beta\leq5$.

In another preferred embodiment, other additional anti-cancer drugs are added during step (a).

In another preferred embodiment, the additional anti-cancer drugs are selected from carboplatin, 5-FU, doxorubicin, CTX, colchicines, or a combination thereof.

In a sixth aspect of the invention, the use of the AMPelopsin salt or its derivatives of the present invention is presented. They are used for the preparation of anti-cancer drugs or can also be used in combination with other anti-cancer drugs to minimize the side effects of these anti-cancer drugs.

MODE OF CARRYING OUT THE INVENTION

Figure 1:
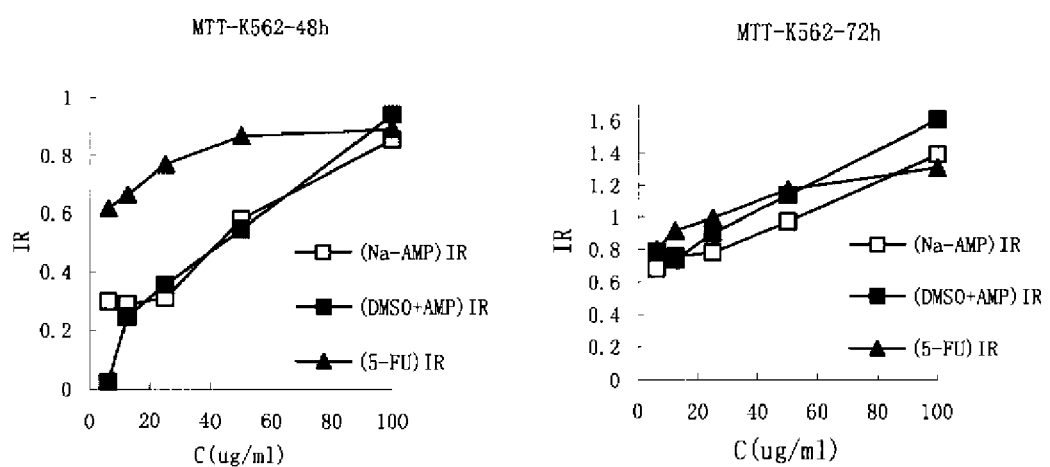
FIG. 1 is a Dose-effect curve showing the impairment of K562 cells following incubation with AMP-Na and AMP-DMSO for 48 h and 72 h.

During broad yet deep research on AMPelopsin, the inventors of the present invention discovered in surprise that the physicochemical properties of AMP can be significantly altered after salifying AMP with weak acid salt of univalent alkali metal ions and modifying the 6 free hydrogen atoms on AMP by unsaturated substitution. When AMP is unmodified or modified by saturated substitution, its solubility will not be altered. It will thus be scarcely dissolved in water or will be gradually precipitated into microcrystallite leading to regional irritation after systemic injection to the human body. In comparison, through unsaturated substitution with univalent cations (eg. at a molar ratio of 2-5 molars of the univalent cations to 1 molar AMP), the water solubility of AMP is significantly improved.

Terms

As used herein, "AMP" refers to AMPelopsin.

As used herein, "AMP-M" refers to AMPelopsin unsaturated salt with univalent cations (abbreviated as AMP-M hereafter) as obtained through partial salification of AMP.

As used herein, "AMPelopsin salt or its derivative" refers to AMPelopsin salt, its hydrate, or solvate.

As used herein, terms "AMPelopsin of the present invention", "AMPelopsin unsaturated salt", "AMPelopsin unsaturated univalent salt" can be used interchangeably, which all refer to the AMP salt after partial substitution of the hydrogen atoms of the 6 hydroxyl groups on AMP. In addition, these terms also refer to the active derivatives of AMP salt (i.e. hydrate or solvate).

As used herein, "AMP-Na$_4$" refers to the AMP salt or its derivatives (i.e. hydrate) with 4 hydrogen atoms of the 6 hydroxyl groups on AMP being substituted by 4 sodium ions.

Salt-Forming Agent

There are no special limits to the types of salt-forming agents used in the present invention. They can be conventionally used strong base weak acid salts, as formed between strong base cations and week acid radicals.

Typical weak acid radicals include but not limited to Ac, $HPO_4$, $H_2PO_4$, $HCO_3$, and $CO_3$, preferably $HCO_3$ and $CO_3$, and more preferably $CO_3$ to reach a stable neural pH range. Typical strong base cations include $Li^+$, $K^+$, $Na^+$, $NH_4^+$, or a combination thereof; preferably $Na^+$.

In another preferred embodiment, the salt-forming agent is selected from sodium bicarbonate, sodium carbonate, or a combination thereof.

Method for Preparation

This present invention provides a method for preparing AMPelopsin salt, which comprises.

(a) reacting AMPelopsin with the salt-forming agent of formula II to form a AMPelopsin salt of formula I $$AMPelopsin + M_mZ \rightarrow C_{15}H_6O_8H_\alpha H_\beta$$

formula II   formula I

Wherein

M is a univalent cation selected from $Li^+$, $K^+$, $Na^+$, $NH_4^+$, or a combination thereof;

Z is an anion selected from $HCO_3^-$, $CO_3^{2-}$, $PO_4^{3-}$, $HPO_4^{2-}$; $H_2PO_4^-$, $Ac^-$, or a combination thereof;

n=1, 2, or 3, $\alpha+\beta=6$, and $2\leq\beta\leq5$.

the molar ratio of AMPelopsin to the salt-forming agent in step (a) is ranged from 1:2 to 1:5, and (b) separating the AMPelopsin salt or its hydrate compound from the reaction system.

Usually, the reaction of step (a) is conducted in aqueous solutions (mixture of water and ethanol) or in water, at a temperature of 4~80° C.

Pharmaceutical Composition

The AMP salt of the present invention can be applied to the treatment of cancers alone or with other drugs. Usually, AMP salt of the present invention can be formulated in non-toxic, inert, and pharmaceutically acceptable water carrier with its pH usually ranged from 5 to 8, and preferably from 6 to 8. The skilled in the art will appreciate that pH value of the solution could be adjusted according to the different properties of the solute and different requirements of any particular cancer treatment. The prepared pharmaceutical composition can be administered by conventional routes, including but not limited to intramuscular, intraperitoneal, intravenous, subcutaneous, intracutaneous or topical administration.

AMP salt of the present invention can be directly used for the treatment of diseases, i.e. for the treatment of cancer. It also can be used in combination with other anti-cancer drugs, such as carboplatin, 5-FU, doxorubicin, CTX, colchicines, or a combination thereof.

The current invention also provides a pharmaceutical composition comprising an effective and safe amount of the AMP salt of the present invention (for example, 0.001-99.9 wt %, and preferably 0.01-90 wt %) and other pharmaceutically acceptable carriers or excipients.

These carriers include but not limited to saline, buffered solution, glucose, water, glycerol, ethanol, and a combination thereof. The pharmaceutical composition shall coordinate with the delivery manner. The pharmaceutical composition of the present invention can be prepared in the injection form, i.e. in normal saline, or in a solution with glucose and other additives by the conventional method. Pharmaceutical compositions in the forms of tablet or capsule can also be prepared by the conventional method. Pharmaceutical compositions in the forms of such as injection, solution, tablet, and capsule are preferred to be prepared under sterile condition. Dose of the active ingredient shall be an effective therapeutic dose, for example, 1 μg-5 mg/kg body weight/day.

A preferred pharmaceutical composition is a pure AMP salt solution with the concentration ranged from 0.2 μg/ml to 500 mg/ml.

In addition, other chemical reagents without pharmacological effects may be optionally added into the pharmaceutical compositions of the present application as pH regulator, stabilizer, or solution adjuvant and so on.

The pharmaceutical compositions of the present application can be subjected to a single or multiple formulations; it can be used alone or in combination with other drugs for the treatment of cancers as an anti-cancer drug and/or enhancer of other anti-cancer drugs.

Advantages of the Present Invention Include:

(a) Improved solubility and desirable stability. Solubility of AMP-M produced by salification is significantly increased and the obtained solution is extremely stable. No turbidity or precipitate is observed within the 15-day storage period. AMP-M can be diluted with clinically widely used PBS at any ratio without alteration of its physicochemical properties and product quality.

(b) Low toxicity. No signs of toxicity are observed following large capacity injection of AMP-M to normal mice. Median lethal dose ($LD_{50}$) of AMP-M is higher than 2 g/kg subsequent to maximum solubility and maximum capacity administration. Comparatively, $LD_{50}$ of AMP is 1 g/kg. Evidently, the toxicity of AMP-M is significantly lower then that of AMP, which suggests its safety application for new drug development.

(c) Joint administration with other anti-cancer drugs. When used in combination with many other anti-cancer drugs, AMP-M serves as a strong enhancer to notably reduce the dose and toxicity of other anti-cancer drugs and correspondingly improve their efficacy. Due to its improved solubility and lowered toxicity, AMP-M is now allowed to be administered at a high dose. Therefore, it is made possible that AMP-M alone be used as an anti-cancer drug in clinical treatment.

More features and benefits of the present invention will become obvious through the following illustrative and non-limiting examples. It is understood that these examples only help exemplify this invention rather than limit the scope of it. The experiments are performed according to common laboratory protocols or the specifications from the manufacturer in case the specific method is not described. Proportion and ratio throughout the invention are by weight, unless otherwise specified.

Example 1

Preparation of AMP-Na and Evaluation of its Solubility and Stability

Different molar ratios of AMP/$NaHCO_3$ were determined to be 1:1, 1:2, 1:3, and 1:4, respectively. AMP was dissolved in 5% ethanol, into which different amount of $NaHCO_3$ and double distilled water were added according to different molar ratios. Dissolution time, solution stability, and pH of the obtained solution were monitored. AMP-Na test solution containing AMP and $Na_2CO_3$ was prepared in water at AMP:$Na_2CO_3$ weight ratios (w/w) of 5:2, 5:3, and 5:4, respectively. The test solution was thereafter diluted 10 times with normal saline or PBS with pH values of 6.0, 6.5, 7.0, 7.4, and 8.0, respectively. Then, pH, clearance, and stability of the solution under different conditions were recorded.

Results:

1. Solubility of AMP Following Salification with $NaHCO_3$

| Ingredients and amount | | Molar ratio of AMP to $NaHCO_3$ | | | | | |
|---|---|---|---|---|---|---|---|
| | | 1:1 | 1:2 | 1:3 | 1:4 | 1:5 | 1:6 |
| AMP (g) | | 0.01 | 0.01 | 0.01 | 0.01 | 0.01 | 0.01 |
| Absolute ethanol (ml) | | 0.5 | 0.5 | 0.5 | 0.5 | 0.5 | 0.5 |
| $NaHCO_3$ (g) | | 0.0026 | 0.0052 | 0.0079 | 0.0105 | 0.0131 | 0.0158 |
| Double distilled water (ml) | | 9.5 | 9.5 | 9.5 | 9.5 | 9.5 | 9.5 |
| result | RT, 4 h* | Transparent with small particles | Transparent with small particles | Transparent with few small particles | Transparent with minimal small particles | Transparent with few small particles | Transparent with small particles |
| | RT, 18 h | dissolved | dissolved | dissolved | dissolved | dissolved | dissolved |
| | RT, 48 h | dissolved | dissolved | dissolved | dissolved | dissolved | dissolved |
| | 4° C., 48 h | dissolved | dissolved | dissolved | dissolved | dissolved | dissolved |
| | pH value | 6.2-6.4 | 6.5-6.7 | 6.7-7.0 | 7.2-7.6 | 7.7-7.9 | 8.1-8.3 |

*Room temperature (RT) is 24° C.

2. Solubility of AMP Following Salification with $Na_2CO_3$

AMP could not be completely dissolved at an AMP/$Na_2CO_3$ ratio (w/w) of 5:2, and tiny particles were found to be precipitated out.

AMP could be completely dissolved at an AMP/$Na_2CO_3$ ratio (w/w) of 5:3. Detailed results are shown in the following table:

| | Test number | | | | | |
|---|---|---|---|---|---|---|
| | 1 | 2 | 3 | 4 | 5 | 6 |
| AMP-Na test solution *(ml) | 0.1 | 0.1 | 0.1 | 0.1 | 0.1 | 0.1 |
| PBS (ml), pH = 6.0 | 0.9 | — | — | — | — | — |
| PBS (ml), pH = 6.5 | — | 0.9 | — | — | — | — |
| PBS (ml), pH = 7.0 | — | — | 0.9 | — | — | — |
| PBS (ml), pH = 7.4 | — | — | — | 0.9 | — | — |

-continued

|  | Test number | | | | | |
|---|---|---|---|---|---|---|
|  | 1 | 2 | 3 | 4 | 5 | 6 |
| PBS (ml), pH = 8.0 | — | — | — | — | 0.9 | — |
| Normal saline (ml) | — | — | — | — | — | 0.9 |
| result  Dissolution at RT * | Dissolved | Dissolved | Dissolved | Dissolved | Dissolved | Dissolved |
| Dissolution at 4° C. (9 d) | Dissolved | Dissolved | Dissolved | Dissolved | Dissolved | Dissolved |
| pH value (2 h) | 7.0 | 7.2 | 7.5 | 8.0 | 8.5 | 8.1 |
| pH value (9 d) | 7.2 | 7.5 | 7.7 | 8.0 | 8.9 | 8.9 |

* AMP-Na test solution: AMP 0.025 g + $Na_2CO_3$ 0.015 g + double distilled water 1 ml.
* Room temperature (RT) is 24° C.

Conclusions:

Pure AMP is a white powder, which does not dissolve in water while dissolves in DMSO. Through salification of AMP with $NaHCO_3$ or $Na_2CO_3$ at certain ratios that yields the AMP-Na solution, solubility of AMP is significantly increased.

Solubility and solution stability of AMP after salification with $NaHCO_3$ and $Na_2CO_3$ are compared. Results demonstrate that an AMP-Na solution containing AMP and $Na_2CO_3$ at a Na:AMP molar ratio of 4:1. AMP could be immediately and completely dissolved herein to obtain a solution with desirable stability. Its solubility is unaltered following dilution with pH 6.0, 6.5, 7.0, 7.4, and 8.0 PBS for 10 times and storage at 4° C. which suggests feasibility for clinical or animal studies.

Example 2

Pharmacological Effects of AMP-Na$_4$ Salt as Compared to AMP

In vitro killing effects of AMP-Na and AMP-DMSO towards human leukemia K562 cells were compared using the MTT assay, which thereby evaluated the difference between AMP-Na formulation and traditional AMP-DMSO solution in terms of pharmacodynamics. After drug exposure for 48 h and 72 h, $IC_{50}$ of AMP-DMSO was determined to be 32.27 μg/m and that of AMP-Na was 29.56 μg/ml, which showed no significant difference in the potency of killing K562 cells in vitro between the two groups.

Materials

AMP powder 0.5 g/vial (purchased from the department of chemistry, Zhongshan Medical University), $Na_2CO_3$ (analytic grade), double distilled water, PBS (pH 6.5 and 7.4), DMSO, 5-FU (purchased from Shanghai Xudong Haipu pharmaceutical company, batch number: H31020593), RPMI 1640 cell culture media, calf serum. MTT, and 10% SDS.

Method for Preparation (1) AMP Na: An AMP-Na solution was prepared according to the method of Example 1 at an AMP:$Na_2CO_3$ ratio (w/w) of 5:3, which was then diluted 10 times with PBS (pH 6.5) to obtain the AMP-Na stock solution. The stock solution was further diluted by PBS (pH 7.4) to the concentration for cell exposure.

(2) AMP-DMSO: AMP was dissolved in 5% DMSO to achieve the concentration for cell exposure.

(3) 5-FU: 5-FU was dissolved in normal saline to achieve the concentration for cell exposure.

All the drug solutions described above were freshly prepared before use, and the final concentration for cell exposure was 100, 50, 25, 12.5, and 6.25 μg/ml, respectively.

Cell Line

Human leukemia K562 cell, purchased from Shanghai Institute of Cell Biology, CAS Cell Culture K562 cells were cultured in RPMI1640 culture media supplemented with 10% calf serum, 100 U/ml of penicillin and streptomycin.

Group Design

Blank control group (solvent+RPMI1640); negative control group (solvent+cell suspension); positive control group (5-FU); AMP-DMSO group; and AMP-Na group.

Experimental

1. K562 cells at their log growth period were collected and centrifuged at 1,000 rpm for 5 minutes. The supernatant was discarded, and the cell density was adjusted to $1 \times 10^5$ cells/ml with RPMI 1640 cell culture media.

2. Ten microliter of the drug solution at various concentrations and 90 μl of the cell suspension or cell culture media were added to each well of the 96-well plate, followed by incubation in a $CO_2$ incubator.

3. Cells were cultured for another 48-hour or 72-hour. Ten microliter of the MTT solution was added to per well 4 hours before the end of the experiment. Then, the solution was discarded and 100 μl of 10% SDS was added for termination of the experiment.

4. The absorbance of the solution was measured at 570 nm using a plate reader after being shaken on a shaker for 10 minutes. Results were printed out and recorded.

Statistical Analysis

The inhibition ratio (%) was calculated from the following equation:

$$\text{Inhibition ratio (\%)} = \frac{(OD_{negative\ control} - OD_{blank\ control}) - (OD_{test\ drug} - OD_{test\ drug\ blank})}{OD_{negative\ control} - OD_{blank\ control}} \times 100\%$$

$IC_{50}$ was calculated by linear regression of drug concentration v.s. cell inhibition ratio.

Results

According to the dose-effect curves of AMP-Na and AMP-DMSO in their killing effects towards K562 cells at 48 h and 72 h, $IC_{50}$ of AMP-DMSO and AMP-Na after cell treatment for 48 h were 32.27 and 29.56 kg/ml, respectively. IC$_{50}$ of AMP-DMSO and AMP-Na after cell treatment for 72 h were 4.09 and 4.23 μg/ml, respectively. There was no significant difference between the killing effects of AMP-Na and AMP-DMSO towards human leukemia K562 cells in vitro (FIG. 1).

| IC$_{50}$ of AMP-DMSO and AMP-Na in killing K562 cells | | | |
|---|---|---|---|
| 48 h | | 72 h | |
| AMP-DMSO | AMP-Na | AMP-DMSO | AMP-Na |
| 32.27 μg/ml | 29.56 μg/ml | 4.09 μg/ml | 4.23 μg/ml |

Conclusions

DMSO was traditionally used to dissolve AMP. However, solubility of AMP in DMSO was low. Moreover, DMSO is unsuitable for clinical use. Besides, DMSO may to some extent interfere the accuracy of the results in both in vivo and in vitro studies. AMP-Na was prepared according to the method of the present invention, and pH value of the solution could be adjusted to 7.4 by PBS (pH 6.5). AMP-Na formulation and AMP-DMSO solution were compared with respect to pharmacodynamics. MTT assay confirmed no significant difference between AMP-Na and AMP-DMSO in the killing effects towards human leukemia K562 cells in vitro following drug treatment for 48 h and 72 h, respectively. Due to its improved water solubility, AMP-Na could be the desirable formulation for AMP, which was ideal for clinical application.

Example 3

Anti-Cancer Effect of AMP-Na$_4$ and its Enhancement of Other Anti-Cancer Drugs

To investigate the anti-cancer effects of AMP-Na and determine the effects to tumor growth thereof when administered alone, and to investigate the synergism of AMP-Na in combination with other anti-cancer drugs, in vivo tumor growth suppression was evaluated for AMP-Na in Sarcoma-180 (S-180) bearing Kunming mice. Single administration of AMP-Na and its joint administration with three other chemotherapeutics (CTX, 5-FU, and carboplatin) were monitored in the present example.

S-180 cells were inoculated subcutaneously to mice at the axillary region at 0.5-1×10$^6$ cells/mouse. AMP-Na was administered on the second day after tumor inoculation. As for joint administration, AMP-Na was intraperitoneally administered to mice 15 minutes after intraperitoneal injection of the chemotherapeutics. The drugs were given 6-8 times in total, one day spaced between two administrations for all the experiments. At the end of experiments, the tumors were removed and weighed, and the tumor inhibition ratio (TIR) was calculated. Pharmaceutical efficacy was considered with TIR≧40% and P<0.05, after statistical analysis. The results showed that AMP-Na alone had no or weak tumor suppression, but significant synergistic action when administered in combination with other anti-cancer drugs. The detailed results are shown as follows:

AMP-Na solution was prepared by the method described in example I. 180 ml of PBS (pH=6.5) was used to adjust pH to 7.2. The prepared solution was filtered through 0.45 and 0.22 μm membrane for sterilization, divided into stock aliquots, and stored at 4° C. for future use. The stock aliquot was further diluted with sterilized PBS (pH=7.4) to the required concentration before drug administration.

5-FU, CTX, and carboplatin solutions were freshly prepared in normal saline before use. Male and female Kunming mice of SPF grade (body weight 18-22 g) were purchased from the Experimental Animal Center (production certificate No. 14-005), Lanzhou University, P. R. China. Mice with the same sex were used in any individual experiment.

S180 cell line was from S180 bearing mice, and was intraperitoneally passaged in Kunming mouse.

Carcinoma inoculation and drug treatment: To each mouse, 0.2 ml of the S180 and H22 cell suspensions (2.5×10$^6$ cells/ml) were subcutaneously injected into the right axillary region (a total of 5×10$^5$ cells per mouse), respectively. On the second day, the animals were grouped at random and drugs were administered accordingly. AMP-Na was i.p. administered at a dose of 50, 75, 112, and 167 mg/kg, respectively, at 0.1 ml/10 g. In the case of joint administration, AMP-Na was i.p. administered 15 minutes after i.p. injection of the chemotherapeutics. The drugs were given once every other day with a total of 6-8 treatments.

Determination of tumor weight and calculation of TIR (tumor inhibition ratio), were as follows. Body weight was recorded on the day after the last drug administration and animals were then sacrificed. The carcinoma was removed and weighed, and TIR (%) was calculated according the following formula:

$$TIR\ (\%) = \frac{\text{carcinoma weight in negative control group (g)} - \text{carcinoma weight in test group (g)}}{\text{carcinoma weight in negative control group (g)}} \times 100\%$$

Standard test of treatment effectiveness: TIR<40% was deemed as ineffective; TIR≧40% and p<0.05 after statistical analysis was considered effective.

Results

1. Synergistic Action of AMP-Na and CTX in Tumor Suppression on S180 Carcinoma in Mice As compared with the positive control, joint administration of AMP-Na and CTX led to a statistically significant reduction in tumor weight. Particularly, joint administration of AMP-Na and CTX at the AMP-Na dose of 50 and 75 mg/kg, respectively, resulted in a significant reduction in tumor weight compared to single administration of CTX. TIR was 7.66, 6.84, −3.86, and −16.25% following single administration of AMP-Na at 50, 75, 112, and 167 mg/kg, respectively. TIR was 64.45, 68.07, 46.13, and 64.52% following joint administration of AMP-Na and CTX at the AMP-Na dose of 50, 75, 112, and 167 mg/kg, respectively. TIR was 53.30% after single administration of CTX.

| Synergistic action of AMP-Na and CTX in tumor suppression on S180 carcinoma | | | | | | |
|---|---|---|---|---|---|---|
| Group | Animal No before/after | Body weight (g) before/after | Days before sacrifice | Tumor weight (g) (X ± SD) | TIR (%) | P value |
| Control (solvent) | 15/14 | 19.80/31.40 | 12 | 1.79 ± 1.17 | | |
| CTX 20 mg/kg, ip | 30/30 | 19.87/28.77 | 12 | 0.84 ± 0.55 | 53.30 | ** |
| AMP-Na 50 mg/kg, ip | 14/13 | 19.86/33.46 | 12 | 1.66 ± 0.84 | 7.66 | |
| AMP-Na 75 mg/kg, ip | 15/15 | 19.93/31.27 | 12 | 1.67 ± 1.03 | 6.84 | |
| AMP-Na 112 mg/kg, ip | 15/15 | 19.87/31.60 | 12 | 1.86 ± 1.21 | −3.86 | |
| AMP-Na 167 mg/kg, ip | 15/14 | 19.93/31.57 | 12 | 2.08 ± 1.07 | −16.25 | |
| CTX + AMP-Na 50 mg/kg, ip | 15/15 | 20.00/28.47 | 12 | 0.64 ± 0.48 | 64.45 | ** |
| CTX + AMP-Na 75 mg/kg, ip | 15/15 | 19.87/29.20 | 12 | 0.57 ± 0.29 | 68.07 | ** |
| CTX + AMP-Na 112 mg/kg, ip | 15/15 | 19.80/29.07 | 12 | 0.97 ± 0.47 | 46.13 | * |
| CTX + AMP-Na 167 mg/kg, ip | 15/14 | 19.80/27.50 | 12 | 0.63 ± 0.33 | 64.52 | ** |

* $p < 0.05$,
** $p < 0.01$

2. Synergistic Action of AMP-Na and 5-FU in Tumor Suppression on S180 Carcinoma

As compared to the positive control, joint administration of AMP-Na and 5-FU led to a statistically significant reduction in tumor weight which showed a dose-dependent TIR. Particularly, joint administration of AMP-Na and 5-FU at the AMP-Na dose of 50, 75, and 112 mg/kg resulted in significant reduction in tumor weight as compared to single administration of 5-FU. TIR was 4.43, 31.28, 33, 49, and 4.45% following single administration of AMP-Na at 50, 75, 112, and 167 mg/kg, respectively. TIR was 57.75, 51.87, 59.21, and 36.65% following joint administration of AMP-Na and 5-FU at the AMP-Na dose of 50, 75, 112, and 167 mg/kg, respectively. TIR was 45.55% following single administration of 5-FU.

3. Synergistic Action of AMP-Na and Carboplatin in Tumor Suppression on S180 Carcinoma As compared to the positive control, joint administration of AMP-Na and carboplatin led to a statistically reduction in tumor weight. Particularly, joint administration of AMP-Na and carboplatin at the AMP-Na dose of 50, 75, 112, and 167 mg/kg, respectively, resulted in significant reduction in tumor weight as compared to single administration of carboplatin. TIR was 23.22, 3.99, 13.87, and −7.47% following single administration of AMP-Na at 50, 75, 112, and 167 mg/kg, respectively. TIR was 65.11, 54.35, 66.37, and 59.26% following joint administration of AMP-Na and carboplatin at the AMP-Na dose of 50, 75, 112, and 167 mg/kg, respectively. TIR was 49.52% after single administration of carboplatin.

| Synergistic action of AMP-Na and 5-FU in tumor suppression on S180 carcinoma | | | | | | |
|---|---|---|---|---|---|---|
| Group | Animal No Before/after | Body weight (g) before/after | Days before sacrifice | Tumor weight(g) (X ± SD) | TIR (%) | P value |
| Control (solvent) | 16/16 | 21.19/33.07 | 11 | 1.98 ± 1.01 | | |
| 5-FU 20 mg/kg, ip | 28/27 | 20.86/29.63 | 11 | 1.08 ± 0.60 | 45.55 | ** |
| AMP-Na 50 mg/kg, ip | 14/14 | 20.86/32.64 | 11 | 1.89 ± 0.75 | 4.43 | |
| AMP-Na 75 mg/kg, ip | 14/14 | 20.79/33.23 | 11 | 1.36 ± 0.69 | 31.28 | |
| AMP-Na 112 mg/kg, ip | 14/14 | 20.86/31.64 | 11 | 1.32 ± 0.78 | 33.49 | |
| AMP-Na 167 mg/kg, ip | 14/14 | 20.86/29.43 | 11 | 1.89 ± 0.59 | 4.45 | |
| 5-FU + AMP-Na 50 mg/kg, ip | 15/15 | 21.13/29.57 | 11 | 0.84 ± 0.46 | 57.75 | ** |
| 5-FU + AMP-Na 75 mg/kg, ip | 15/15 | 21.07/29.73 | 11 | 0.95 ± 0.46 | 51.87 | ** |
| 5-FU + AMP-Na 112 mg/kg, ip | 15/15 | 21.00/28.73 | 11 | 0.81 ± 0.45 | 59.21 | ** |
| 5-FU + AMP-Na 167 mg/kg, ip | 15/14 | 20.93/28.57 | 11 | 1.26 ± 0.55 | 36.65 | * |

* $p < 0.05$,
** $p < 0.01$

Synergistic action of AMP-Na and carboplatin in tumor suppression on S180 carcinoma

| Group | Animal No. before/after | Body weight (g) before/after | Days before sacrifice | Tumor weight (g) (X ± SD) | TIR (%) | P value |
|---|---|---|---|---|---|---|
| Control (solvent) | 15/15 | 18.93/30.07 | 10 | 1.46 ± 0.52 | | |
| carboplatin 25 mg/kg, ip | 28/28 | 18.57/25.75 | 10 | 0.74 ± 0.28 | 49.52 | ** |
| AMP-Na 50 mg/kg, ip | 14/14 | 18.71/31.00 | 10 | 1.12 ± 0.30 | 23.22 | |
| AMP-Na 75 mg/kg, ip | 14/13 | 18.64/31.38 | 10 | 1.40 ± 0.58 | 3.99 | |
| AMP-Na 112 mg/kg, ip | 14/13 | 18.57/29.69 | 10 | 1.26 ± 0.69 | 13.87 | |
| AMP-Na 167 mg/kg, ip | 14/11 | 18.58/29.55 | 10 | 1.57 ± 0.71 | −7.47 | |
| carboplatin + AMP-Na 50 mg/kg, ip | 15/15 | 19.07/23.00 | 10 | 0.51 ± 0.16 | 65.11 | ** |
| carboplatin + AMP-Na 75 mg/kg, ip | 15/14 | 18.80/24.14 | 10 | 0.67 ± 0.20 | 54.35 | ** |
| carboplatin + AMP-Na 112 mg/kg, ip | 15/15 | 18.73/21.60 | 10 | 0.49 ± 0.22 | 66.37 | ** |
| carboplatin + AMP-Na 167 mg/kg, ip | 15/13 | 18.80/22.08 | 10 | 0.59 ± 0.22 | 59.26 | ** |

\* p < 0.05,
\*\* p < 0.01

Conclusions:

Intraperitoneal injection of AMP-Na in combination with CTX, 5-FU, and carboplatin can produce synergistic effect on tumor suppression of S180 carcinoma in mice. Joint administration of AMP-Na with 5-FU, CTX, and carboplatin at the AMP-Na dose of 50-167 mg/kg could lead to a statistically significant antitumor effect as compared to single administration of 5-FU, CTX, and carboplatin in terms of reduction of tumor weight in S-180 bearing mice. Joint administration of AMP-Na with these anticancer drugs at a dose of 75-112 mg/kg shows the most significant effect on tumor weight reduction.

Example 4

Toxicity Study of AMP-Na$_4$

The acute toxicity of AMP-Na in mice was studied to determine the LD50 and maximum tolerable dose (MTD) in comparison to those of AMP.

AMP-Na was intravenously administered to Kunming mice. Dominant signs of toxicity and mortality were observed within the 7-day period. Major organs of dead animals were removed, fixed, and subject to pathological study. Results showed that $LD_{50}$ of AMP-Na in both male and female mice via intravenous administration was above 2000 mg/kg, and $LD_0$ was above 1000 mg/kg. In comparison, $LD_{50}$ of AMP-DMSO was 1000 mg/kg, which demonstrated reduced toxicity of AMP after salification.

1.25 g $Na_2CO_3$ was added to 5 ml of AMP-PEG solution at an AMP:$Na_2CO_3$ (w/w) ratio of 5:3. Normal saline (36.25 ml) and 37% HCl (0.75 ml) were added to obtained the AMP stock solution with a concentration of 50 mg/ml and pH of 7.3 (concentrations of solvents including PEG 400, propanediol, and ethanol were 0.03, 0.0445, and 0.015 g/ml, respectively). The final AMP-Na solution had a pH value of 7.3. The stock solution was further diluted in normal saline to the required concentration, and was i.v. or i.p. administered to mice at 0.2 ml/10 g bodyweight.

Both male and female Kuming mice of SPF grade, weighing 18-22 g, were used in the experiment. The mice were purchased from the Experimental Animal Center (production certificate No. 14-005), Lanzhou University, P. R. China. Solvent group for AMP-Na and different AMP-Na serial doses groups were tested (detailed information for grouping was listed in the Results portion). All data were analyzed by DAS software.

Results

Motality of mice after i.v. injection of AMP-Na at 1000 mg/kg for one time (n = 10)

| AMP-Na dose (mg/kg) | | 1-3 h | Day 1 | Day 2 | Day 3 | Day 4 | Day 5 | Day 6 | Day 7 | Total death |
|---|---|---|---|---|---|---|---|---|---|---|
| 1000 | ♀ | 0 | 0 | 0 | 0 | 0 | 0 | 0 | 0 | 0 |
| | ♂ | 0 | 0 | 0 | 0 | 0 | 0 | 0 | 0 | 0 |
| Solvent | ♀ | 0 | 0 | 0 | 0 | 0 | 0 | 0 | 0 | 0 |
| | ♂ | 0 | 0 | 0 | 0 | 0 | 0 | 0 | 0 | 0 |

Motality of mice after i.v. injections of AMP-Na for two times at a total dose of 2000 mg/kg (n = 10)

| AMP-Na dose (mg/kg)/injection time/interval | | 1-3 h | Day 1 | Day 2 | Day 3 | Day 4 | Day 5 | Day 6 | Day 7 | Total death |
|---|---|---|---|---|---|---|---|---|---|---|
| 2000/2/5 h | ♀ | 0 | 0 | 0 | 1 | 1 | 1 | 0 | 0 | 3 |
|  | ♂ | 0 | 0 | 0 | 0 | 0 | 0 | 0 | 0 | 0 |
| Solvent/2/5 | ♀ | 0 | 0 | 0 | 0 | 0 | 0 | 0 | 0 | 0 |
|  | ♂ | 0 | 0 | 0 | 0 | 0 | 0 | 0 | 0 | 0 |

Motality of mice after i.v. injection of AMP-DMSO at 1000 mg/kg (n = 10)

| AMP-DMSO dose (mg/kg)/injection time/interval | | 1-3 h | Day 1 | Day 2 | Day 3 | Day 4 | Day 5 | Day 6 | Day 7 | Total death |
|---|---|---|---|---|---|---|---|---|---|---|
| 1000 | ♀ | 0 | 1 | 2 | 2 | 0 | 0 | 0 | 0 | 5 |
|  | ♂ | 0 | 1 | 1 | 2 | 1 | 0 | 0 | 0 | 5 |
| Solvent | ♀ | 0 | 0 | 0 | 0 | 0 | 0 | 0 | 0 | 0 |
|  | ♂ | 0 | 0 | 0 | 0 | 0 | 0 | 0 | 0 | 0 |

Conclusions $LD_{50}$ of AMP-Na via i.v. injection in mice was >2000 mg/kg. Specifically, maximal tolerance dose (MTD) was >2000 mg/kg in male mice; $LD_0$ via i.v. was >1000 mg/kg. $LD_{50}$ of AMP-DMSO was 1000 mg/kg.

Example 5

Chemical Structure Analysis of AMPelopsin Sodium Salt

AMP-Na as prepared in example 1 with the molecular formula of $C_{15}H_8O_8Na_4 \cdot 5H_2O$ was subject to chemical structure analysis.

[Thermogravimetric Analysis]

A weight loss of 3.41% and 12.31% was observed for AMP-Na when heated from 20 to 80.2° C. and from 80.2 to 176.0° C., respectively. The total weight loss of 15.72% primarily accorded with the theoretic calculation value for a compound containing 4.5 molar of water per molar of AMP-Na. An endothermic at 119.6° C. was also detected in the differential scanning calorimeter (DSC) thermogram, which indirectly verified the existence of crystal water in its chemical structure.

[Elemental Analysis]

The measured contents of carbon and hydrogen in AMP were 35.87% and 3.66%, respectively, which primarily matched with the theoretic calculation value (C 36.16% and H 3.64%).

[Ionic Chromatographic Analysis]

The measured content of Na was 18.6%, which primarily accorded with the theoretic calculation (18.46%).

[Ultraviolet Absorption Spectrum]

Ultraviolet absorption spectrum of AMP-Na in water demonstrated an E band with 4 absorption peaks at 204.6, 206.1, 210.1, and 218.4 nm which corresponded to the aromatic ring. An absorption peak at 328.3 nm was observed at B band which showed a 36.1 nm of red shift when compared with that of AMP (depleted of Na) in methanol.

[Nuclear Magnetic Resonance (NMR)]

Equipment: Varian$^{UNITY}$ INOVA 500 Superconducting pulse FTIR (USA)
(1) $^1$H NMR
Analysis by $^1$H NMR
Solvent: DMSO

| Peak number | Chemical shift δ of AMP (ppm) | Chemical shift δ of AMP-Na (ppm) | Chemical shift δ of AMP-Na neutralized to pH 6.0 (ppm) | Split peak number | Proton number | Remark |
|---|---|---|---|---|---|---|
| a | 4.45 | 4.05 | 4.41 | d | 1 | 3 CH |
| b | 4.94 | 4.49 | 4.90 | d | 1 | 2 CH |
| c | 5.73 |  | 5.73 | br s | 1 | 3 OH |
| d | 5.90 | 5.05 | 5.86 | d | 1 | 8 CH |
| e | 5.94 | 5.07 | 5.90 | d | 1 | 6 CH |
| f | 6.45 | 6.28 | 6.44 | s | 2 | 2'/6' CH |
| g | 8.16 | 8.29 | 8.30 | br s | 1 | 4' OH |
| h | 8.89 |  | 8.88 | br s | 2 | 3'/5' OH |
| i | 10.82 |  | 10.90 | br s | 1 | 7 OH |
| j | 11.87 | 12.3(br s) | 11.88 | s | 1 | 5 OH |

-continued

(2) $^{13}$C NMR
Analysis by $^{13}$C NMR

| Peak number | Chemical shift δ of AMP (ppm) (solvent: DMSO) | Chemical shift δ of AMP-Na (ppm) (solvent: D$_2$O) | Multiplicity (DEPT) | Carbon number | Remark |
|---|---|---|---|---|---|
| A | 71.83 | 71.64 | d | 1 | 3 CH |
| B | 83.40 | 83.72 | d | 1 | 2 CH |
| C | 95.16 | 97.92 | d | 1 | 8 CH |
| D | 96.20 | 99.05 | d | 1 | 6 CH |
| E | 100.65 | 99.82 | s | 1 | 10 C |
| F | 107.19 | 107.50 | d | 2 | 2'/6' CH |
| G | 127.37 | 126.34 | s | 1 | 1' C |
| H | 133.63 | 137.29 | s | 1 | 4' C |
| I | 145.86 | 147.61 | s | 2 | 3'/5' C |
| J | 162.66 | 161.72 | s | 1 | 9 C |
| K | 163.49 | 162.84 | s | 1 | 5 C |
| L | 166.95 | 163.46 | s | 1 | 7 C |
| M | 197.58 | 194.04 | s | 1 | C=O |

Note:
Due to low solublility of AMP-Na in DMSO, D$_2$O was used as the solvent.

Interpretation of $^1$H NMR and $^{13}$C NMR Spectra:
(1) In the spectrum of AMP-Na, chemical shift at 12.3 (1H, br s) ppm indicated formation of intra-molecular hydrogen bond between position 5 hydroxyl proton and position 4 oxygen.
(2) Compared to the $^1$H NMR spectrum of AMP, absorption peaks at position 3 OH, position 7 OH, and position 3'/5' OH disappeared in that of AMP-Na.
(3) Compared to the $^{13}$C NMR spectrum of AMP, a shift of 2-3 ppm was observed at position 8 CH, position 6 CH, position 4'C, position 3'/5' C, position 7 C, and the C=O group in that of AMP-Na.
(4) Chemical shift of all the hydrogen atoms in the $^1$H NMR spectrum of AMP-Na after neutralized to pH 6.0 was similar to that of AMP.

The above results indicated that no structural alteration was induced for rings A, B and C after formation of AMP-Na. Hydrogen atoms at position 2 and 3 were preserved and intra-molecular hydrogen bond was formed between the hydroxyl proton at position 5 and the oxygen at position 4. Therefore, it was suggested that hydrogen atoms on the OH at positions 3, 7, 3', and 5' were substituted by Na.

The molecular formula of AMP-Na was $C_{15}H_8O_8Na_4\cdot 5H_2O$; its relative molecular weight is: 498.03; and its molecular structure is:

[Chemical structure diagram of AMP-Na with 5H$_2$O]

Example 6

Preparation of Amp-Na (Case II)

The steps in Example 1 was repeated, with NaHCO$_3$ being replaced by Na$_2$HPO$_4$ at a molar ratio of 1:2 (AMP:Na$_2$HPO$_4$). The same AMP-Na salt was formed with the molecular formula of $C_{15}H_8O_8Na_4\cdot 5H_2O$.

Similarly, solubility and solution stability of the resulted AMP-Na was notably improved.

Example 7

Preparation of AMP-Na (case III)

The steps in Example 1 was repeated, with NaHCO$_3$ being replaced by NaAc at a molar ratio of 1:4 (AMP:NaAc). The same AMP-Na salt was formed with the molecular formula of $C_{15}H_8O_8Na_4\cdot 5H_2O$.

Similarly, solubility and solution stability of the resulted AMP-Na was notably improved.

Example 8

Pharmaceutical Composition Containing Amp-Na

The following pharmaceutical composition was prepared:

| | |
|---|---|
| AMP-Na (C$_{15}$H$_8$O$_8$Na$_4$•5H$_2$O) | 500 mg |
| 50 mM PBS (pH 6.8) | 50 ml |

The pharmaceutical composition can be used for the suppression of cancer growth.

Example 9

Compound Pharmaceutical Composition Containing AMP-Na

The following compound pharmaceutical composition was prepared:

| | |
|---|---|
| AMP-Na (C$_{15}$H$_8$O$_8$Na$_4$•5H$_2$O) | 500 mg |
| CTX | 25 mg |
| 50 mM PBS (pH 6.8) | 50 ml |

This compound pharmaceutical composition can be used to reduce the side effect of CTX as a result of the synergistic action between AMP-Na and CTX.

The invention claimed is:

1. AMPelopsin salt and its derivatives, wherein the hydrogen atoms of the six hydroxyl groups on AMPelopsin are partially substituted by 2-5 univalent cations.

2. The AMPelopsin salt and its derivatives of claim 1, wherein the molecular formula of AMPelopsin is as shown in formula I:

$$C_{15}H_6O_8H_\alpha M_\beta \qquad (I)$$

wherein M is a univalent cation selected from Li$^+$, K$^+$, Na$^+$, NH$_4^+$ or a combination thereof;

$\alpha+\beta=6$, and $2\leq\beta\leq5$.

3. The AMPelopsin salt and its derivatives of claim 2, wherein M is Na.

4. The AMPelopsin salt and its derivatives of claim 3, wherein the AMPelopsin salt is a dihydrate or pentahydrate of the AMPelopsin sodium salt.

5. The AMPelopsin salt and its derivatives of claim 4, wherein the pentahydrate has the following structure:

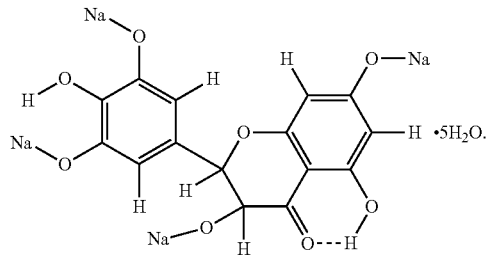

6. A method for preparing the AMPelopsin salt and its derivatives of claim 1, wherein the method comprises the following steps:
   (a) reacting AMPelopsin with a salt-forming agent of formula II to form a AMPelopsin salt of formula I $$AMPelopsin + M_mZ \rightarrow C_{15}H_6O_8H_\alpha M_\beta$$

formula II    formula I wherein M is a univalent cation selected from Li$^+$, K$^+$, Na$^+$, NH$_4^+$ or a combination thereof;

Z is an anion selected from HCO$_3^-$, CO$_3^{2-}$, PO$_4^{3-}$, HPO$_4^{2-}$, H$_2$PO$_4^-$, Ac$^-$, or a combination thereof;

m=1, 2, or 3;

$\alpha+\beta=6$, and $2\leq\beta\leq5$;

the molar ratio of AMPelopsin to M in the salt-forming agent in step (a) is ranged from 1:2 to 1:5; and (b) separating the AMPelopsin salt or its hydrate.

7. The method of claim 6, wherein the salt-forming agent is selected from sodium bicarbonate, sodium carbonate or a combination thereof.

8. A pharmaceutical composition comprising AMPelopsin salt or its derivatives of claim 1 and pharmaceutically acceptable salt.

9. The pharmaceutical composition of claim 8, further comprising additional anti-cancer drug(s).

10. A method for preparing a pharmaceutical composition comprising:
   (a) mixing AMPelopsin of formula I and its derivatives $$C_{15}H_6O_8H_\alpha M_\beta \qquad (I)$$

wherein M is a univalent cation selected from Li$^+$, K$^+$, Na$^+$, NH$_4^+$ or a combination thereof;

$\alpha+\beta=6$, and $2\leq\beta\leq5$;

with pharmaceutically acceptable carriers to form the pharmaceutical composition.

* * * * *